(12) United States Patent
Das et al.

(10) Patent No.: US 10,927,133 B2
(45) Date of Patent: Feb. 23, 2021

(54) PROCESS FOR THE PREPARATION OF IXAZOMIB CITRATE

(71) Applicant: SUN PHARMACEUTICAL INDUSTRIES LIMITED, Maharashtra (IN)

(72) Inventors: Prasenjit Prafulla Das, Rajasthan (IN); Santosh Richhariya, Madhya Pradesh (IN); Hashim Nizar Poovanathil Nagoor Meeran, Kerala (IN); Mohan Prasad, Haryana (IN)

(73) Assignee: SUN PHARMACEUTICAL INDUSTRIES LIMITED, Maharashtra (IN)

( * ) Notice: Subject to any disclaimer, the term of this patent is extended or adjusted under 35 U.S.C. 154(b) by 0 days.

(21) Appl. No.: 16/643,427

(22) PCT Filed: Aug. 24, 2018

(86) PCT No.: PCT/IB2018/056458
§ 371 (c)(1),
(2) Date: Feb. 28, 2020

(87) PCT Pub. No.: WO2019/043544
PCT Pub. Date: Mar. 7, 2019

(65) Prior Publication Data
US 2020/0190117 A1 Jun. 18, 2020

(30) Foreign Application Priority Data
Sep. 2, 2017 (IN) .............................. 201711031158

(51) Int. Cl.
*C07F 5/02* (2006.01)

(52) U.S. Cl.
CPC .................................... *C07F 5/025* (2013.01)

(58) Field of Classification Search
None
See application file for complete search history.

(56) References Cited

U.S. PATENT DOCUMENTS

| 7,714,159 | B2 | 5/2010 | Pickersgill et al. |
| 8,859,504 | B2 | 10/2014 | Elliott et al. |
| 9,175,018 | B2 * | 11/2015 | Elliott ........................ A61P 7/06 |
| 2016/0031913 | A1 | 2/2016 | Elliott et al. |

FOREIGN PATENT DOCUMENTS

| CN | 106478701 A | 3/2017 | |
| CN | 106986884 * | 7/2017 | |
| WO | WO-2005097809 A2 * | 10/2005 | ......... C07K 5/06191 |
| WO | 2016/155684 A1 | 10/2016 | |
| WO | 2017/046815 A1 | 3/2017 | |

OTHER PUBLICATIONS

Flick et al., "Synthetic Approaches to the New Drugs Approved During 2015," J. Med. Chem. 60: 6580-6515 (2017).
International Search Report in PCT/IB2018/056458 dated Dec. 27, 2018.
Written Opinion of the International Searching Authority in PCT/IB2018/056458 dated Dec. 27, 2018.

* cited by examiner

*Primary Examiner* — Amy C Bonaparte
(74) *Attorney, Agent, or Firm* — Medler Ferro Woodhouse Mills PLLC

(57) ABSTRACT

The present disclosure provides a process for the preparation of ixazomib citrate.

8 Claims, No Drawings

PROCESS FOR THE PREPARATION OF IXAZOMIB CITRATE

FIELD OF THE INVENTION

The present disclosure provides a process for the preparation of ixazomib citrate.

BACKGROUND OF THE INVENTION

Ixazomib citrate is chemically designated as 1,3,2-dioxaborolane-4,4-diacetic acid, 2-[(1R)-1-[[2-[(2,5-dichlorobenzoyl)amino]acetyl]amino]-3-methylbutyl]-5-oxo-, depicted by Formula I.

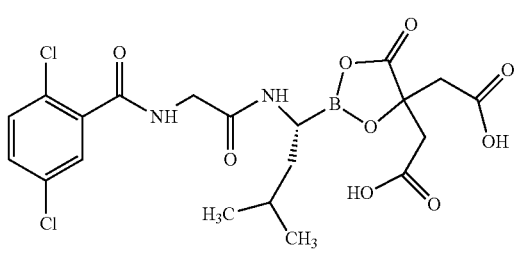

Formula I

Ixazomib citrate is a proteasome inhibitor indicated in combination with lenalidomide and dexamethasone for the treatment of patients with multiple myeloma who have received at least one prior therapy.

U.S. Pat. Nos. 8,859,504 and 9,175,017; PCT Publication Nos. WO02016/155684 and WO2017/046815; and CN106478701A disclose processes for the preparation of ixazomib citrate of Formula I.

There is a need for an alternate and improved process for the preparation of ixazomib citrate of Formula I.

SUMMARY OF THE INVENTION

The present disclosure provides an efficient, industrially feasible process for the preparation of ixazomib citrate of Formula I, optionally which the process can occur in a single pot.

DETAILED DESCRIPTION OF THE INVENTION

Various embodiments and variants of the present disclosure described hereinafter.

The term "single pot process" or "process in a single pot" refers to a process wherein all reaction steps mentioned are conducted in a single reaction vessel.

The term "about," as used herein, refers to any value which lies within the range defined by a variation of up to ±10% of the value.

A first aspect of the present disclosure provides a process for the preparation of ixazomib citrate comprising:

a) reacting a compound of Formula II

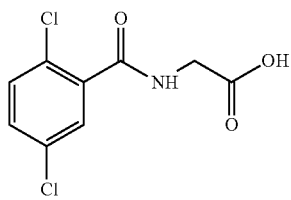

Formula II with a compound of Formula III

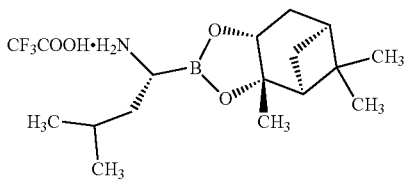

Formula III in the presence of a coupling agent;
b) adding hydrochloric acid and (2-methylpropyl)boronic acid in a polar protic solvent to (a); and
(c) adding citric acid monohydrate to (b), wherein ixazomib citrate is obtained. In some embodiments, the process is a single pot process.

In some embodiments, the compound of Formula II can be prepared by following the procedures provided in art, for example, U.S. Pat. No. 8,859,504.

In some embodiments, the compound of Formula III can be prepared by following the procedures provided in art, for example, U.S. Pat. No. 7,714,159.

In some embodiments, the compound of Formula II reacts with the compound of Formula III in the presence of a solvent.

In some embodiments, the solvent is selected from dichloromethane, chloroform, carbon tetrachloride, diethyl ether, acetone, tetrahydrofuran, and combinations thereof. In some embodiments, the solvent is dichloromethane.

In some embodiments, the compound of Formula II reacts with the compound of Formula III at about −5° C. to about 10° C., for example, at about 0° C. to about 5° C.

In some embodiments, the coupling agent is selected from dicyclohexylcarbodiimide (DCC), 1-(3-dimethylaminopropyl)-3-ethylcarbodiimide hydrochloride (EDC.HCl), benzotriazol-1-yloxytris(dimethylamino)phosphonium hexafluorophosphate (BOP), and combinations thereof. In some embodiments, the coupling agent is EDC.HCl.

In some embodiments, the compound of Formula II reacts with the compound of Formula III in a base.

In some embodiments, the base is selected from pyridine, trimethylamine, triethylamine, diethylamine, diisopropylethylamine, triethanolamine, morphine, N-methyl morphine, and combinations thereof. In some embodiments, the base is diisopropylethylamine.

In some embodiments, the reaction mixture of (a) obtained after reacting in the presence of the coupling agent can be stirred, quenched with water, worked up, or any combination thereof. In some embodiments, the reaction mixture is then concentrated under reduced pressure to obtain an oily concentrate.

In some embodiments, a lower alcohol, e.g., methanol, followed by addition of a hexane solvent to the oily concentrate can be performed. In some embodiments, the mixture is further stirred. In some embodiments, the resulting mixture is treated with 1N hydrochloric acid and (2-methylpropyl)boronic acid in a polar protic solvent to provide a reaction mixture which can be further reacted with citric acid monohydrate to provide ixazomib citrate.

In some embodiments, the term polar protic solvent can be selected from methanol, ethanol, propanol, butanol, water, and mixtures thereof.

In some embodiments, the ixazomib citrate can be isolated by filtration, decantation, extraction, distillation, evaporation, chromatography, precipitation, concentration, crystallization, centrifugation, or recrystallization. In some embodiments, the ixazomib citrate can be dried under reduced pressure, by air drying, or vacuum tray drying.

In some embodiments, the present disclosure provides ixazomib citrate with yield of more than 70%, more than 75%, more than 80%, more than 85%, or more than 90%.

In some embodiments, the present disclosure provides ixazomib citrate with chromatographic (HPLC) purity of more than 95%, more than 98%, more than 99%, more than 99.5%. more than 99.7%, more than 99.9%, or more than 99.95%.

While the present disclosure has been described in terms of its specific aspects and embodiments, certain modifications and equivalents will be apparent to those skilled in the art and are intended to be included within the scope of the present invention.

Method:

Chromatographic purity of the sample was determined by HPLC instrument using "Waters® 2996 Alliance® HPLC with PDA detector and HPLC column XBridge C8 (150× 4.6) mm, 3.5 μm.

The following example is for illustrative purposes only and should not be construed as limiting the scope of the invention in any way.

EXAMPLE

Example 1

Preparation of Ixazomib Citrate

The compound of Formula II (30 g) and dichloromethane (600 mL) were added into a flask at 25° C. to obtain a reaction mixture. The reaction mixture was cooled to 0° C. to 5° C. under stirring, and the compound of Formula III (51.91 g) it was added, followed by addition of EDC.HCl (52.59 g). Diisopropylethylamine (54 g) was dissolved in dichloromethane (150 mL) and added to the reaction mixture drop-wise in about 120 minutes at 0° C. to 5° C. with stirring. Deionized water (720 mL) was then added into reaction mixture and stirred for about 15 minutes. The reaction mixture was then separated into two layers. The organic layer was washed with potassium carbonate solution (400 mL, 2% v/v potassium carbonate in water) followed by washing with orthophosphoric acid (400 mL, 1% w/v orthophosphoric acid in water) and finally washed with sodium chloride solution (400 mL, 10% w/v sodium chloride in water). The solvents from the reaction mixture were distilled out under reduced pressure to obtain an oily concentrate.

Methanol (600 mL) was added into the oily concentrate (80 g), followed by the addition of hexane (600 mL) at 25° C. with stirring to obtain a reaction mixture. 1N HCl solution (245 mL) was added into the reaction mixture at 10° C. to 15° C., followed by the addition of (2-methylpropyl)boronic acid (36.99 g). The reaction mixture was heated to 25° C. and stirred for 24 hours. The reaction mixture was allowed to settle and separate into two layers. The aqueous layer containing product was washed with hexane (200 mL). Dichloromethane (300 mL) was added to the aqueous layer, followed by the addition of deionized water (900 mL) to obtain a reaction mixture. Sodium hydroxide solution (90 mL, 20% w/v sodium hydroxide in water) was added into the reaction mixture and stirred for 15 minutes. The reaction mixture was allowed to settle and separated into two layers. The aqueous layer was again washed with dichloromethane (200 mL). The aqueous layer was heated to 35° C. and citric acid monohydrate (160 g) was added into it and stirred for 3 hours at 25° C. The reaction mass was filtered and solid obtained was washed with deionized water (60 mL) to obtain the title product.

Yield: 50 g (1.66 w/w, 79.6%)
Chromatographic Purity: 99.96%

We claim:
1. A process for preparing ixazomib citrate comprising:
a) reacting a compound of Formula II

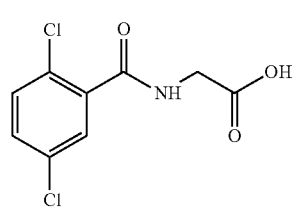

Formula II with a compound of Formula III

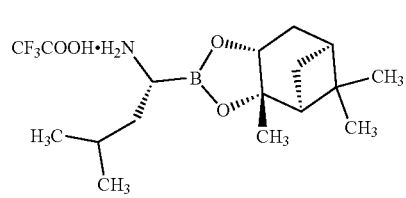

Formula III in the presence of a coupling agent;
b) adding hydrochloric acid and (2-methylpropyl)boronic acid in a polar protic solvent to the reaction mixture of (a); and
c) adding citric acid monohydrate to the reaction mixture of (b),
wherein (a), (b), and (c) occur in a single pot process, and wherein ixazomib citrate is obtained.

2. The process according to claim 1, wherein the coupling agent is selected from dicyclohexylcarbodiimide (DCC), 1-(3-dimethylaminopropyl)-3-ethylcarbodiimide hydrochloride (EDC.HCl), benzotriazol-1-yloxytris(dimethylamino)phosphonium hexafluorophosphate (BOP), or combinations thereof.

3. The process according to claim 1, wherein the coupling agent is 1-(3-dimethylaminopropyl)-3-ethylcarbodiimide hydrochloride.

4. The process according to claim 1, wherein the reacting in (a) is carried out in a solvent selected from dichloromethane, chloroform, carbon tetrachloride, diethyl ether, acetone, tetrahydrofuran, or combinations thereof.

5. The process according to claim 1, wherein the reacting in (a) is carried out in a base selected from pyridine, trimethylamine, triethylamine, diethylamine, diisopropylethylamine, triethanolamine, morphine, N-methyl morphine, or combinations thereof.

6. The process according to claim 1, wherein the reacting in (a) is carried out at about −5° C. to about 10° C.

7. The process according to claim 1, wherein the polar protic solvent in (b) is selected from methanol, ethanol, propanol, butanol, water, or a mixture thereof.

8. The process according to claim 1, wherein the ixazomib citrate has HPLC purity of more than 99.5%.

\* \* \* \* \*